United States Patent
Freeman

(10) Patent No.: US 10,952,706 B2
(45) Date of Patent: Mar. 23, 2021

(54) ULTRASOUND SYSTEMS WITH MICROBEAMFORMERS FOR DIFFERENT TRANSDUCER ARRAYS

(71) Applicant: KONINKLIJKE PHILIPS N.V., Eindhoven (NL)

(72) Inventor: Steven Russell Freeman, Seattle, WA (US)

(73) Assignee: Koninklijke Philips N.V., Eindhoven (NL)

(*) Notice: Subject to any disclaimer, the term of this patent is extended or adjusted under 35 U.S.C. 154(b) by 251 days.

(21) Appl. No.: 15/774,116

(22) PCT Filed: Nov. 23, 2016

(86) PCT No.: PCT/EP2016/078522
§ 371 (c)(1),
(2) Date: May 7, 2018

(87) PCT Pub. No.: WO2017/089376
PCT Pub. Date: Jun. 1, 2017

(65) Prior Publication Data
US 2018/0317888 A1 Nov. 8, 2018

Related U.S. Application Data

(60) Provisional application No. 62/259,121, filed on Nov. 24, 2015.

(51) Int. Cl.
*A61B 8/14* (2006.01)
*A61B 8/00* (2006.01)
(Continued)

(52) U.S. Cl.
CPC .............. *A61B 8/54* (2013.01); *A61B 8/145* (2013.01); *A61B 8/4444* (2013.01);
(Continued)

(58) Field of Classification Search
None
See application file for complete search history.

(56) References Cited

U.S. PATENT DOCUMENTS 5,678,554 A 10/1997 Hossack et al.
5,997,479 A 12/1999 Savord et al.
(Continued)

FOREIGN PATENT DOCUMENTS

EP 2666547 A2 11/2013
WO 2011089537 A1 7/2011
(Continued)

*Primary Examiner* — Joel F Brutus

(57) ABSTRACT

An ultrasound microbeamformer for one or more transducer arrays includes a plurality of channels, each of which has two transmitters and a receiver which is selectively coupled to two or more transducer elements by T/R switches and dynamically switchable receive switches (RXSW). The transmitters enable different transducers to be actuated differently, such as transmitting a high frequency pulse or waveform with one transmitter and a low frequency pulse or waveform with the other transmitter. The transmitters may both be used during the same transmit-receive cycle to simultaneously transmit and receive both high and low frequency signals for the formation of a common image.

13 Claims, 4 Drawing Sheets

(51) Int. Cl.
    *G01S 15/89*      (2006.01)
    *G01S 7/52*      (2006.01)
    *A61B 8/08*      (2006.01)

(52) U.S. Cl.
    CPC .......... *A61B 8/4477* (2013.01); *A61B 8/4494* (2013.01); *A61B 8/5207* (2013.01); *A61B 8/56* (2013.01); *G01S 7/5208* (2013.01); *G01S 7/52095* (2013.01); *G01S 15/8915* (2013.01); *G01S 15/8927* (2013.01); *G01S 15/8952* (2013.01); *G01S 15/8956* (2013.01)

(56) References Cited

U.S. PATENT DOCUMENTS

| | | | |
|---|---|---|---|
| 8,330,332 | B2 | 12/2012 | Weekamp et al. |
| 8,512,250 | B2 | 8/2013 | Quistgaard |
| 2006/0058677 | A1* | 3/2006 | Okada ................ G01S 15/8963 600/459 |
| 2008/0208061 | A1 | 8/2008 | Halmann |
| 2008/0229835 | A1 | 9/2008 | Davidsen et al. |
| 2010/0298713 | A1* | 11/2010 | Robinson ............ G01S 15/8909 600/459 |
| 2013/0172757 | A1 | 7/2013 | Frigstad et al. |
| 2014/0058293 | A1 | 2/2014 | Hynynen et al. |
| 2014/0330126 | A1 | 11/2014 | Kang et al. |
| 2015/0080727 | A1 | 3/2015 | Specht et al. |
| 2015/0099977 | A1* | 4/2015 | Kim .................... G01S 15/8925 600/447 |
| 2015/0241397 | A1* | 8/2015 | Savord ................. G01S 7/5208 600/459 |
| 2015/0264747 | A1* | 9/2015 | Abbott ................. H05B 3/141 392/407 |
| 2015/0293223 | A1 | 10/2015 | Park et al. |

FOREIGN PATENT DOCUMENTS

| | | |
|---|---|---|
| WO | 2015026787 A2 | 2/2015 |
| WO | 2016083985 A1 | 6/2016 |

\* cited by examiner

ULTRASOUND SYSTEMS WITH MICROBEAMFORMERS FOR DIFFERENT TRANSDUCER ARRAYS

This application is the U.S. National Phase application under 35 U.S.C. § 371 of International Application No. PCT/EP2016/078522, filed on Nov. 23, 2016, which claims the benefit of Provisional Application Ser. No. 62/259,121, filed Nov. 24, 2015. These applications are hereby incorporated by reference herein.

This disclosure relates to medical diagnostic ultrasound systems and, in particular, to ultrasound systems with microbeamformers for different transducer probe arrays, such as multi-frequency transducer probes.

The images made by pulse-echo ultrasound systems are formed using the echoes returned from the transmission of ultrasonic pulses or waves into the body. The ultrasound thus makes a round-trip from the probe to a point in the image field from which an echo is reflected back to the probe. The time of the round-trip provides the spatial location of the echo signal in the image. The ultrasonic energy of the pulse and its echoes are constantly attenuated and scattered by the tissue through which they travel, which requires good sensitivity for the reception of low-level echo signals. The attenuation is not uniform for all ultrasound signals, however. Higher frequencies are attenuated more rapidly with their passage through tissue. Higher frequencies, moreover, produce the best resolution and hence better images. All things being equal, it would be preferable to use higher frequency probes for all imaging, but the more rapid attenuation of higher frequency ultrasound mandates that the higher imaging frequencies are only used for shallow imaging of depths of a few centimeters. For greater depths such as are necessary for most abdominal imaging, lower frequency probes are used which will image at greater depths but with less image resolution. Efforts have been made to work around this physical limitation, such as zone focusing. In zone focusing, a first image is acquired at shallow depth with high frequency ultrasound focused at the shallow depth. Then, a second image is acquired at a deeper depth with lower frequency ultrasound focused at the deeper depth. The two "zones," shallow and deep, are then displayed joined together as one image extending over the full depth range. The combined image will exhibit good resolution at the shallow depth where higher frequencies were used, and a greater depth than the high frequency image alone but with lesser resolution by the addition of the deeper, low frequency image. But a consequence of this technique is that it requires the acquisition of two images, which doubles the time to acquire a full image and hence halves the frame rate of display of real time imaging. Accordingly it would be desirable to have a probe that can image at both shallow and deeper depths and without the frame rate penalty of multi-zone focused imaging.

In some aspects, the present disclosure provides ultrasound systems that can include an ultrasound probe including a first array of transducer elements, a second array of transducer elements, and a microbeamformer application-specific-integrated-circuit (ASIC), located in the probe and coupled to the first and second arrays of transducer elements. The microbeamformer ASIC includes a plurality of channels. Each channel can include a first transmitter coupled to a transducer element of the first array, a second transmitter coupled to a transducer element of the second array, and a receiver selectively coupled to the transducer element of the first array, the transducer element of the second array, or both. In some aspects, the first array can include high frequency transducer elements and the second array can include low frequency transducer elements. The receiver can be selectively coupled to the transducer element of the first array by a first transmit/receive (T/R) switch, and selectively coupled to the transducer element of the second array by a second T/R switch. The first and second T/R switches can be selectively coupled to each other by a third switch (RX-SWB). And, a fourth switch (RXSWNXT) can be included and configured to selectively couple a receiver of one channel to a receiver of another channel of the plurality of channels of the microbeamformer ASIC.

In certain aspects, the receiver can include a TGC amplifier and/or a time delay. The first and second transmitters can include high voltage transmitters, respectively, and the receiver can include a low voltage receiver. The first and second T/R switches can include switches configured to be dynamically closed during reception of echo signals by the transducer elements. The first and second arrays of transducer elements can both extend in an azimuth direction and are located adjacent to each other in an elevation direction. A third array of transducer elements can extend in the azimuth direction and be located adjacent to the first array on an opposite side as the second array, and the second transmitter can be coupled to a transducer element of the third array. The first array of transducer elements can be mounted at a first distal end of the probe, and the second array of transducer elements can be mounted at a second distal end of the probe. The first array mounted on one side of the probe can include high frequency transducer elements and the second array mounted on a different side of the probe can include low frequency transducer elements. The probe can include control logic configured to selectively operate the first and second T/R switches and the third switch (RX-SWB). The control logic and the first and second transmitters can be configured to selectively operate in response to channel data provided by a main ultrasound system.

In accordance with the principles of the present disclosure, an ultrasound probe has a microbeamformer ASIC (application-specific integrated circuit) configured to transmit ultrasound from different arrays. For example, the microbeamformer ASIC can be used to transmit and receive echo signals from a plurality of arrays in an ultrasound probe. The plurality of arrays can include, e.g., a curved array, a sector array, and/or a linear array. The different arrays can operate at different frequencies, e.g., at both high and low frequencies. Transmission of the multiple frequencies can be generated from different arrays sequentially or simultaneously. For example, one array can transmit higher frequency ultrasound at one point in time and a second array can transmit lower frequency ultrasound at a later point in time. In some embodiments, the higher and lower frequency ultrasound can be transmitted at the same time. In some examples, probe implementations are described with both a dedicated high frequency transducer and a dedicated low frequency transducer and with high and low frequency transducer elements actuated simultaneously during the same transmit-receive cycle. The ultrasound systems described herein, e.g., enable a clinician to perform both high and low frequency imaging with the same probe, and to form well resolved images over the full depth of field in a single transmit-receive cycle and at a high frame rate of display.

It is noted that high and low frequency are generally described in relation to each other, so a high frequency array will transmit a higher center frequency than a low frequency array that transmits a lower center frequency. Arrays of transducer elements are configured to transmit and receive ultrasound over a bandwidth associated with a particular center frequency. For example, "high frequency" can range from 3-7 MHz (80% bandwidth at a 5 MHz center frequency). "Low frequency" can range from 2-4.5 MHz (78% bandwidth at 3.2 MHz center frequency. Other ranges are available, but the two frequency ranges can overlap so that echoes of interest can be received by arrays with different frequency characteristics. Similarly, "high voltage" refers to voltages in the tens of volts, such as voltages greater than +30V or less than −30V. In some instances, high voltage devices are +35V or −35V supplies. "Low voltage" refers to voltages in the single digits, such as 1.5V to 5V. In some instances, the low voltages are 3.3V or 5V.

Figure 1:
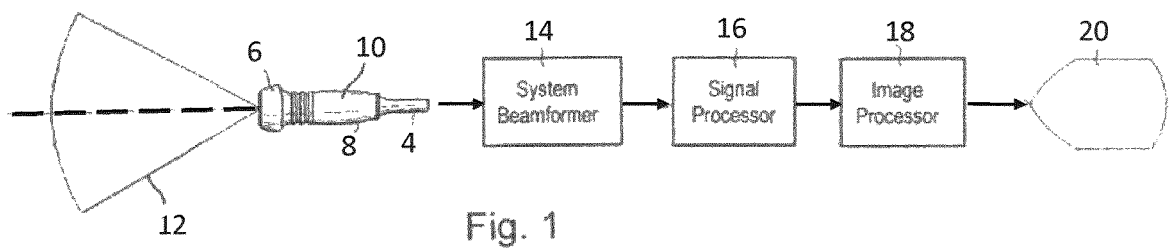
FIG. 1 illustrates in block diagram form an ultrasonic diagnostic imaging system constructed in accordance with the principles of the present disclosure.

Referring first to FIG. 1, an ultrasound system constructed in accordance with the principles of the present disclosure is shown in block diagram form. An ultrasound probe 10 is provided which is to be held by its handle section 8 against the body of a patient to image the anatomy below the point of contact. An array transducer at the distal end 6 of the probe transmits focused pulses or waves along directions referred to as beam directions over a two or three dimensional region of the body. This region is shown as a sector-shaped plane 12 in FIG. 1. Echoes are returned from tissue, blood and structures along the beam direction in response to each transmission and the echoes are processed by beamforming to form a series of image signals received from along the beam. The image region 12 is scanned in this manner with a sequence of adjacent beams to acquire image signals over the full image region, and these signals are further processed by detection and scan conversion to create an image of the anatomy of the image region.

The probe 10 contains a microbeamformer ASIC to which the elements of the transducer array are coupled, which is described in further detail below. The microbeamformer stimulates the elements of the array to transmit the desired beams and also receives and processes the echoes received by the transducer elements to form coherent echo signals. The microbeamformer may perform all of the receive beamforming, or may do partial beamforming which is completed by a system beamformer 14. The main ultrasound system can be contained with the probe on the same or separate circuitry, or the main ultrasound system can be a separate unit coupled to the probe via a cable. As shown, the probe is connected to the main system by a cable 4, which couples control signals from the main system to the microbeamformer in the probe, and also couples the beamformed receive signals from the microbeamformer to the system beamformer. After the received signals have been fully beamformed they are coupled to a signal processor 16 which performs functions such as decimation, filtering, harmonic separation, and signal compounding. The processed signals are coupled to an image processor 18 which forms them into images by processes such as amplitude or Doppler detection and scan conversion. The formed images are displayed on an image display 20.

Figure 2:
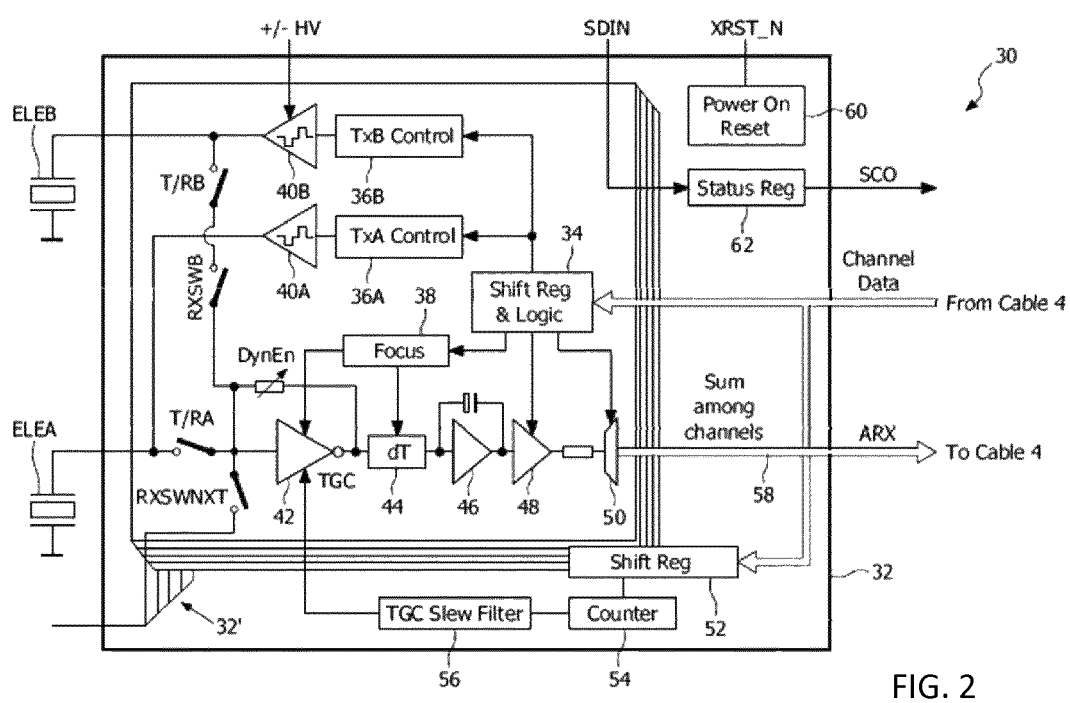
FIG. 2 illustrates in block diagram form a channel of a microbeamformer ASIC which transmits and receives ultrasound at multiple frequencies.

A microbeamformer ASIC 30 of the present disclosure is shown in block diagram form in FIG. 2. The microbeamformer is constructed as a plurality of channels 32, one of which is shown in the drawing. Other identical channels are represented at 32'. Each channel can control one or more elements of a transducer array. In the implementation of FIG. 2, the illustrated channel 32 is shown controlling two transducer elements, ELEA and ELEB. A shift register and logic circuit 34 receives channel data from the main system, which instructs the channel how to transmit ultrasound and process received ultrasound signals for the image desired by the clinician. The channel data controls two transmit control circuits 36A and 36B, which determine the nature of the transmitted pulse or waveform, e.g., its frequency, and the times at which each transmit control circuit transmits a pulse or waveform. The appropriate waveforms are amplified by high voltage transmitters 40A and 40B and the high voltage transmit signals are applied to the transducer elements ELEA and ELEB. A portion of the channel data is used to control receive circuitry of the channel including a focus control circuit 38. The focus control circuit 38 enables a TGC amplifier 42 to begin amplifying received echo signals from one or more of the transducer elements coupled to the channel. The focus control circuit also sets the delay to be applied to received echo signals by a delay circuit 44 for proper focusing of the received signals in combination with echo signals received by other channels of the microbeamformer 30. The gain applied by the TGC amplifier as echoes are received from increasing depths along the beam is controlled by TGC circuitry. A portion of the channel data is loaded into a shift register 52 which is used by a counter 54 to condition a TGC slew filter 56. The resultant TGC signal is used to dynamically control the gain of the TGC amplifier as echoes are received from a transducer element. The TGC circuitry thus applies a time gain control signal in accordance with the TGC characteristic chosen by the clinician.

The amplified and delayed receive signals are buffered by the amplifier 46 for application to a cable driver 48 which generates a voltage to drive a conductor of the cable 4. A multiplexer 50 directs the channel output signals to an appropriate microbeamformer output line 58 where they are summed together with the receive signals of other channels as necessary for beamforming. A sum signal ARX is coupled to the main system over a conductor of the cable 4.

The microbeamformer can include a power on reset circuit 60 which resets the microbeamformer to an initial state when power is first applied to the microbeamformer. A status register 62 accumulates status data from the channels which is returned to the system as SCO data to inform the main ultrasound system as to the operational status of the microbeamformer 30.

The microbeamformer channel 32 has two transmit/receive (T/R) switches T/RA and T/RB which are used to protect the input of the TGC amplifier 42 by opening the connections between the transducer elements and the TGC amplifier when the transmitters 36A and 36B are applying high voltage transmit signals to the transducer elements. The T/R switches also serve to select the receive signals from the two elements for receive processing. When T/RA is closed, receive signals from ELEA are coupled to the TGC amplifier 42. When T/RB and RXSWB are closed, receive signals from ELEB are couples to the TGC amplifier. When all three of these switches are closed, signals received by both transducer elements are coupled to the TGC amplifier. A fourth switch, RXSWNXT, is closed to couple signals received by ELEA and/or ELEB to the receive circuitry of other channels, where they may be processed in combination with signals received from other transducer elements. This RXSWNXT switch also enables signals received on other channels to be coupled to the input of TGC amplifier 42 for summation and concurrent processing with signals received by elements ELEA and/or ELEB on that channel.

Figure 3:
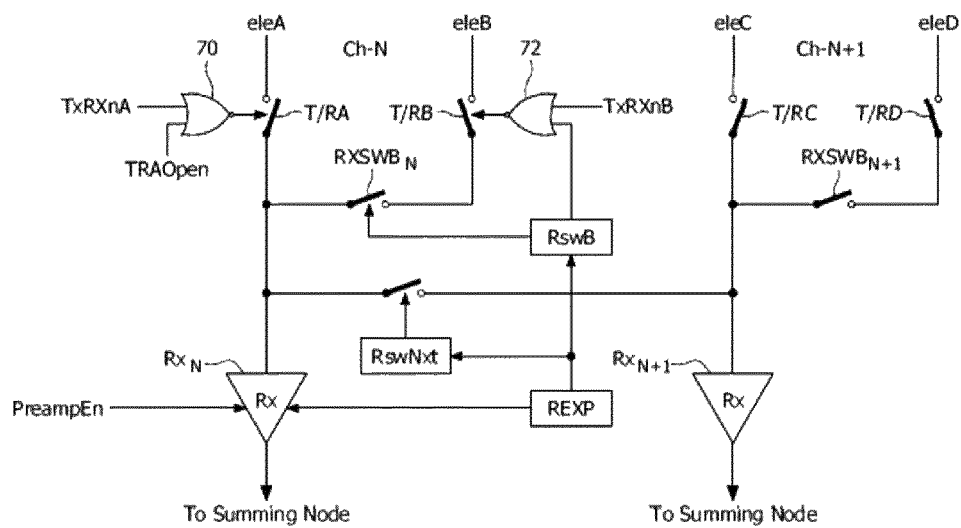
FIG. 3 illustrates in block diagram form the receive configuration of the microbeamformer ASIC of FIG. 2.

FIG. 3 shows the receive signal circuitry of two microbeamformer channels to illustrate how the signals received by more than two transducer elements may be combined and processed by the microbeamformer. The left channel Ch-N is coupled to two transducer elements, eleA and eleB. The T/R switches T/RA and T/RB are controlled by logic gates 70 and 72 to open when the high voltage transmitters (not shown) pulse the elements to transmit ultrasound, and close the T/R switches after transmission when echo signals are to be received. Either one or both of the T/R switches may be closed to select one or both of the elements for reception. For instance, when echoes are to be received only from element eleA, only the T/RA switch is closed during reception. When echoes are to be received only from element eleB, the T/RB switch and the RXSWB$_N$ switch (under control of RswB logic) are closed and switch T/RA is left open. Reception can commence with only one element, with the second element coupled in during reception for dynamic expansion of the receive aperture as echoes are received from deeper in the body. For reception by both elements, all three switches are closed to couple received signals to preamplifier Rx (e.g., the TCG amplifier 42) which is enabled for receive signal processing by an enable signal PreampEn. The time at which the preamplifier Rx of the channel begins to process received signals is controlled by the REXP logic.

A switch RXSWNXT is controlled by RswNxt logic when it is desired to combine echo signals from eleA and/or eleB with echo signals from other channels, or to process their signals through preamplifiers of other channels. A continuing series of RXSWNXT switches between channels enables echo signals of eleA and/or eleB to be directed to any other channel of the microbeamformer. The illustrated RXSWNXT switch can be closed to couple echo signals from eleA and/or eleB to the preamplifier of the second channel shown, Ch-N+1, for processing by its preamplifier RxN+1 alone or in combination with echo signals from elements eleC and eleD. So for instance, reception can begin with echo signals from element eleA with echo signals from eleB coupled in later, followed by the later addition of echo signals from element eleC and then element eleD with the closure of switch RXSWBN followed by switch RXSWB$_{N+1+}$. The initial stage of the high voltage T/R(A-D) switches would have been closed at the beginning of receive. Depending on the relative orientation of the elements in the array, this operation can facilitate dynamically expanding apertures in the azimuth direction, in elevation, or both. With no delay applied in this process, it can be useful for expanding aperture in elevation where the array has a lens to generate a receive focus in the field of view. The outputs of the preamplifiers are coupled to summing nodes for combining after time delay with other signals from other channels, such as the illustrated summing node line 58 in FIG. 2.

In certain aspect, the present disclosure describes a beamforming architecture that can be used to operate two or more different arrays operating at different frequencies. In some embodiments, a first array of transducer elements can be positioned on the same end of a probe as a second array, and the first array can operate at higher frequencies while the second array operates at lower frequencies. In certain embodiments, the first array can be positioned on an opposing side of the probe as the second array which points sound in a different direction than the first array. In some embodiments, three or more arrays can be positioned at different locations with respect to each other on a probe enclosure. Each of the arrays in such an instance can be configured to operate at different frequencies. For example, the first array can operate a lower frequency than the second and third array, and the second array can operate at a lower frequency than the third array. This flexibility in arranging the arrays in different positions and with different frequencies is enabled by the microbeamformer ASIC described herein.

Figure 4:
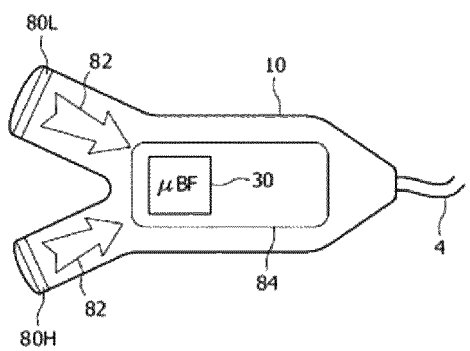
FIG. 4 illustrates an ultrasound probe with dedicated high and low frequency transducers.

FIG. 4 illustrates a dual frequency probe 10 which can be implemented using the microbeamformer of FIGS. 2 and 3. The probe 10 has two distal ends, one mounting a low frequency array transducer 80L and the other mounting a high frequency array transducer 80H. The arrays are coupled to a microbeamformer ASIC 30 located on a printed circuit board 84 in the handle of the probe. Each array is coupled to the microbeamformer by an interposer 82 which is coupled to the elements of an array at one end and to the ASIC 30 at the other end. Interposers are well known in the art as described in US patent publication no. 2008/0229835 (Davidsen et al.) and U.S. Pat. No. 8,330,332 (Weekamp et al.) In some implementations flex circuit can also be used to connect the transducer elements to the microbeamformer ASIC. The clinician can press one distal end of the probe against the skin of the patient and perform low frequency imaging, and can simply reposition the probe to press the other distal end against the patient to perform high frequency imaging, all without the need to change probes. The microbeamformer channels can operate both arrays simultaneously, using one transmitter of each channel to drive the high frequency array 80H and the other transmitter of each channel to drive the low frequency array 80L. Images from both arrays can be displayed on the display screen 20, or only images from a selected transducer can be displayed. When the clinician presses the "Select" button on the control panel to select one of the transducers, the T/R switches for a particular set of elements, i.e., low frequency or high frequency elements, are closed during receive to direct echo signals received by the selected set of elements to the system beamformer 14, the signal processor 16, and the image processor 18 for display of a desired image on the display screen. Other selection approaches can be used. For example, in some embodiments, the image processor 18 can be used to automatically identify which array is active by determining which array is generating an image due to being positioned on a patient for scanning.

An alternative probe configuration is to locate the high and low frequency arrays side-by-side in the distal end 6 of a probe with one distal end such as probe 10 shown in FIG. 1.

Figure 5A:
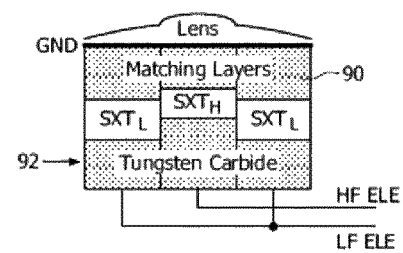
FIGS. 5a and 5b illustrate a single transducer array with both high and low frequency transducer elements suitable for operation with a multi-frequency microbeamformer ASIC of the present disclosure.
Figure 5B:
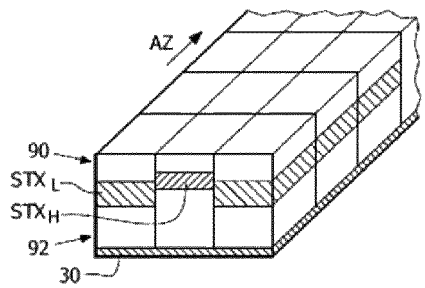

Another probe implementation of the present disclosure is shown in FIGS. 5a and 5b, in which a central high frequency array of elements SXT$_H$ is driven by one transmitter of a microbeamformer channel 32, and the other transmitter of the channel drives two elevationally positioned rows of low frequency elements SXT$_L$ which are located on either side of the central array. FIG. 5a is a cross-sectional view through an elevational plane of the transducer arrays showing low frequency elements SXT$_L$ located on either side of a high frequency element SXT$_H$. The rows of elements extend in the azimuth direction as shown in FIG. 5b. The high and low frequency elements are of different shapes, sizes, and/or aspect ratios as shown in the drawings, with the high frequency elements SXT$_H$ being thinner than the low frequency elements $SXT_L$ in this example. On top of the elements are matching layers 90 which match the transducer element impedances to the impedance of a human body. A ground plane GND overlays the matching layers which are electrically conductive to ground the top electrodes of the transducer elements for patient safety. An acoustic lens of a polymeric material overlays the ground plane. The bottom electrode of the high frequency transducer elements is coupled a high frequency transmitter of a microbeamformer channel by a conductor HF ELE, and the bottom electrodes of the low frequency transducer elements are to the low frequency transmitter of the channel by a conductor LF ELE. This connection is made with tungsten carbide interposers 92 which, together with the matching layer thicknesses, equalize the height of the transducer stack for the different size transducer elements.

The transducer elements can be coupled to an ASIC in a variety of ways. In some embodiments, the transducer elements can be coupled to a flex circuit behind the array (e.g., conductors HF ELE and LF ELE), which is coupled to a connector and a PCB housing an ASIC. In some embodiments, the transducer elements can be mounted on the microbeamformer ASIC 30 as shown in FIG. 5b. In some instances, flip-chip technology can be used in mounting the array to the microbeamformer. The electrical connections, which also bond the microbeamformer ASIC to the transducer stack, may be formed by solder bump bonding or with conductive epoxy to bond pads of the ASIC.

In some embodiments, both the high and low frequency arrays can be operated at a single transmit receive interval to form images which take advantage of the performance characteristics of the low and high frequency arrays. Since separate transmitters are used for the low and high frequency elements, the transmit timing of both types of arrays can be slightly offset so that the high and low frequency arrays are both transmit focused at the same depth of field. Echoes received by the high frequency array can be used to form the image in the near field, and as echoes are received from greater depths, the low voltage RXSW switches for the low frequency array elements can be dynamically closed to supplement the high frequency reception with echoes from the low frequency elements, thereby extending the depth of field of the image beyond what is possible with the high frequency array alone. Thus, an image which takes advantage of both high and low frequencies during the same transmit-receive cycle can provide an image which exhibits good near field resolution and extended depth of field and without any penalty in frame rate of display.

What is claimed is:

1. An ultrasound probe comprising:
   a first array of transducer elements mounted at a first distal end of the ultrasound probe;
   a second array of transducer elements mounted at a second distal end of the ultrasound probe; and
   a microbeamformer application-specific-integrated-circuit (ASIC), located in the ultrasound probe and coupled to the first array of transducer elements and the second array of transducer elements, the microbeamformer ASIC comprising a plurality of channels, wherein each channel comprises a first transmitter coupled to a first transducer element of the first array, a second transmitter coupled to a second transducer element of the second array, and a receiver selectively coupled to the first transducer element of the first array, the second transducer element of the second array, or both.

2. The ultrasound probe of claim 1, wherein the first array comprises high frequency transducer elements and the second array comprises low frequency transducer elements.

3. The ultrasound probe of claim 1, wherein the receiver is selectively coupled to the first transducer element of the first array by a first transmit/receive (T/R) switch, and is selectively coupled to the second transducer element of the second array by a second T/R switch.

4. The ultrasound probe of claim 3, wherein the first T/R switch and the second T/R switch are configured to be dynamically closed during reception of echo signals by the transducer elements.

5. The ultrasound probe of claim 3, wherein a third switch (RXSWB) is configured to be dynamically closed during reception of echo signals by the first transducer element of the first array and second transducer element of the second array.

6. The ultrasound probe of claim 5, further comprising a fourth switch (RXSWNXT) configured to selectively couple a receiver of one channel to a receiver of another channel of the plurality of channels of the microbeamformer ASIC.

7. The ultrasound probe of claim 5, comprising control logic configured to selectively operate the first T/R switch, the second T/R switch and the third switch (RXSWB).

8. The ultrasound probe of claim 7, wherein the control logic and the first transmitter and the second transmitter are configured to selectively operate in response to channel data provided by a main ultrasound system.

9. The ultrasound probe of claim 1, wherein the receiver further comprises a TGC amplifier.

10. The ultrasound probe of claim 9, wherein the receiver further comprises a time delay.

11. The ultrasound probe of claim 1, wherein the first transmitter and the second transmitter each comprise high voltage transmitters.

12. The ultrasound probe of claim 1, wherein the first array of transducer elements and the second array of transducer elements both extend in an azimuth direction.

13. The ultrasound probe of claim 1, wherein the first array comprises high frequency transducer elements and the second array comprises low frequency transducer elements.

* * * * *